United States Patent
Lee et al.

(10) Patent No.: US 7,118,881 B2
(45) Date of Patent: Oct. 10, 2006

(54) MICRO/NANO-FABRICATED GLUCOSE SENSORS USING SINGLE-WALLED CARBON NANOTUBES

(75) Inventors: Junghoon Lee, Seoul (KR); JaeHyun Chung, Evanston, IL (US); Kyong-Hoon Lee, Wilmette, IL (US)

(73) Assignee: Northwestern University, Evanston, IL (US)

( * ) Notice: Subject to any disclaimer, the term of this patent is extended or adjusted under 35 U.S.C. 154(b) by 119 days.

(21) Appl. No.: 10/729,854

(22) Filed: Dec. 5, 2003

(65) Prior Publication Data
US 2005/0124020 A1 Jun. 9, 2005

(51) Int. Cl.
*C12Q 1/54* (2006.01)
(52) U.S. Cl. .................. 435/14; 435/25; 977/DIG. 1
(58) Field of Classification Search ............... 435/14, 435/25; 977/DIG. 1
See application file for complete search history.

(56) References Cited

U.S. PATENT DOCUMENTS

| | | | |
|---|---|---|---|
| 6,528,020 B1 | 3/2003 | Dai et al. | |
| 2002/0117659 A1 | 8/2002 | Lieber et al. | |
| 2003/0217928 A1 | 11/2003 | Lin et al. | |
| 2005/0130296 A1* | 6/2005 | Pisharody et al. | 435/287.2 |
| 2005/0230270 A1* | 10/2005 | Ren et al. | 205/777.5 |
| 2006/0021881 A1* | 2/2006 | Soundarrajan et al. | 205/777.5 |

OTHER PUBLICATIONS

Gao M. et al. Glucose Sensors Based on Glucose Oxidase Containing Polypyrrole Aligned Carbon Nanotube Coaxial Nanowire Electrodes. Synthetic Metals 137(1-3) 1393-1394, 2003.*
Davis, J. et al. Chemical and Biochemical Sensing with Modified Single Walled Carbon Nanotubes. Chem Eur J 9(16)3732-3739, Aug. 18, 2003.*
Azamian B. et al. Bioelectrochemical Single Walled Carbon Nanotubes. JACS 124(43) 12664-12665, Oct. 3, 2002.*
Besteman, Koen; Lee, Jeong-O; Wiertz, Frank G.M.; Heering, Hendrik, A.; Dekker, Cees. Enzyme-Coating Carbon Nanotubes as Single-Molecule Blosensors. Department of Nanosciences and DIMES, Delft University of Technology, Lorentzweg 1, 2628 CJ Delft, The Netherlands; Nano Letters. May 1, 2003, vol. 3, No. 6, pp. 727-730.
Zhao, Wei; Song, Chulho; Pehrasson, Pehr E.. Water Soluable and Optically pH Sensitive Single-Walled Carbon Nanotubes from Surface Modification. Department of Chemistry, University of Arkansas, 2801 South University Avenue, Little Rock, Arkansas, 72204 and Chemistry Division, Naval Research Laboratory, Washington, DC 20375-5000; JACS. 2002, vol. 124, pp. 12418-12419.
Jijun Zhao, et al.; "Gas Molecule Adsorption in Carbon Nanotubes and Nanotube Bundles", NANOTECHNOLOGY, Mar. 14, 2002, UK, vol. 13; pp. 195-200; Institute of Physics Publishing; PII: S0957-4484(02)30254-.
Yuehe Lin, et al.; "Glucose Biosensors Based on Carbon Nanotube Nanoelectrode Ensembles", Nano Letters, Feb. 2004, vol. 4, No. 2; pp. 191-195; Copyright 2004 by the American Chemical Society.
Koen Besteman, et al.; "Enzyme-Coated Carbon Nanotubes as Single-Molecule Biosensors", Nano Letters, 2003, vol. 3, No. 6; pp. 727-730; Copyright 2003 by the American Chemical Society.
Collins, Philip G., et al.; "Extreme Oxygen Sensitivity of Electronic Properties of Carbon Nanotubes", Northwestern University Library Database: MAS Ultra—School Edition, Mar. 10, 2000, vol. 287, Issue 5459, EBSCO Host Research Database Website.
Jing Li, et al.; "Carbon Nanotube Sensors for Gas and Organic Vapor Detection", Nano Letters, 2003, vol. 3, No. 7; pp. 929-933; Copyright 2003 by the American Chemical Society.
Shu Peng, et al.; "Toward Large Arrays of Multiplex Functionalized Carbon Nanotube Sensors for Highly Sensitive and Selective Molecular Detection", Nano Letters , 2003, vol. 3, No. 3; pp. 347-351; Copyright 2003 by the American Chemical Society.
Krupke, Ralph, et al.; "Separation of Metallic from Semiconducting Single-Walled Carbon Nanotubes", Northwestern University Library Database: MAS Ultra—School Edition, Jul. 18, 2003, vol. 301, Issue 5631, EBSCO Host Research Database Website.
Pavel Nikolaev, et al.; "Gas-Phase Catalytic Growth of Single-Walled Carbon Nanotube from Carbon Monoxide", Chemical Physics Letters 313 (1999) 91-97, Nov. 5, 1999; Copyright 1999 Elsevier Science B.V. al. Society.

* cited by examiner

*Primary Examiner*—Ralph Gitomer
(74) *Attorney, Agent, or Firm*—Reinhart Boerner Van Deuren, S.C.

(57) ABSTRACT

A novel glucose sensor utilizing hydrogen-specific gas sensing capability of single walled carbon nanotubes assembled on microelectrodes. Highly specific glucose sensing was demonstrated using buffered sample solutions with clinically significant concentrations. The approach enables a simple but powerful bio-sensor reliably operating with a completely new principle, and opens up novel device applications where functional nano-components can be integrated into a bioMEMS device.

7 Claims, 7 Drawing Sheets

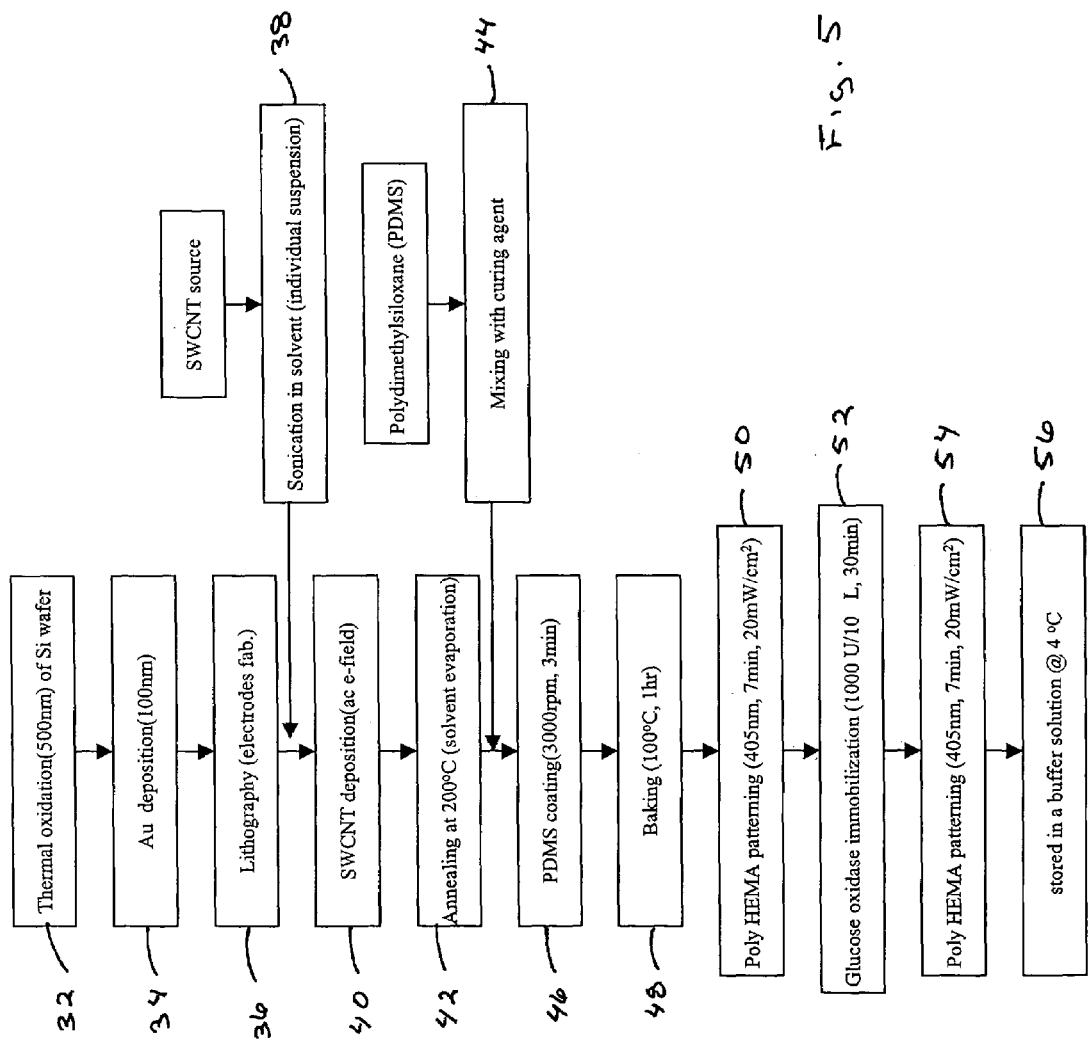

MICRO/NANO-FABRICATED GLUCOSE SENSORS USING SINGLE-WALLED CARBON NANOTUBES

BACKGROUND OF THE INVENTION

Glucose sensing is a critical step towards the timely diagnosis and treatment of diabetes, which is one of the major diseases with great clinical attentions. There have been intensive research and well-developed commercialized products to easily and accurately monitor a blood glucose level. Non-invasive or minimally invasive glucose monitoring has been considered as one of the vital concerns for clinical applications, due to the need of frequent monitoring and the inconveniences of blood sampling. Therefore, a simpler and more reliable approach is desired, especially in terms of the sensitivity to a very small-volume body fluid.

Carbon nanotube devices have been employed in a range of chemical and biological sensor applications. See, U.S. Pat. No. 6,528,020, the entirety of which is incorporated herein by reference. However, such devices are described in the '020 patent only in the most general terms. Glucose sensing, for example, is mentioned prospectively, without regard to device configuration or mode of operation. The search for a reliable, accurate glucose sensor continues to be a concern in the art. More recently and in more detail, carbon nanotubes, have been proposed for potentially high-sensitivity monitoring of glucose, but overall performance and sufficient specificity for practical applications remain to be proven. [K. Besteman, J. Lee, F. G. M. Wiertz, H. a. Heering, and C. Dekker, "Enzyme-Coated Carbon Nanotubes as Single-Molecule Biosensors," *Nano lett.*, vol. 3, pp. 727–730, 2003.]

BRIEF DESCRIPTION OF THE DRAWINGS

FIG. 5. Schematically, a detailed process for fabrication of certain sensors/apparatus of this invention.

SUMMARY OF THE INVENTION

Figure 1:
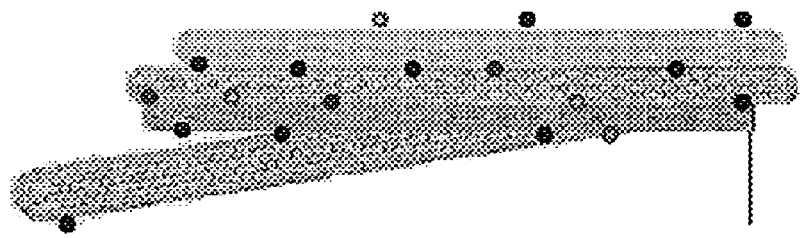
FIG. 1. Conceptual illustration of chemical and physical sorption of $H_2$(•) on SWCNT bundles.

In light of the foregoing, it is an object of the present invention to provide various carbon nanotube sensors and/or devices and method(s) for sensing glucose or determining glucose concentration, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide an assembly or configuration of single-walled carbon nanotubes (SWCNTs) such that the interstitial spaces or sites thereof can be used to sense or detect hydrogen gas in conjunction with the presence of glucose.

It is an object of the present invention to provide a chemical or biological system for use in conjunction with the aforementioned nanotube assembly/configuration, such a system producing directly or indirectly hydrogen gas in an amount related to a particular analyte to be sensed, measured and/or monitored by the nanotube assembly/configuration.

It is also an object of the present invention to provide a sensor, apparatus and/or method for measuring or monitoring glucose levels quickly at clinically-significant levels.

Other objects, features, benefits and advantages of the present invention will be apparent from this summary and its descriptions of various embodiments, and will be readily apparent to those skilled in the art having knowledge of carbon nanotube devices and assembly/fabrication techniques. Such objects, features, benefits and advantages will be apparent from the above as taken into conjunction with the accompanying examples, data, figures and all reasonable inferences to be drawn therefrom, alone or with consideration of the references incorporated herein.

The present invention relates, generally, to a glucose sensor apparatus employing the hydrogen-specific gas sensing capability of SWCNTs assembled on microelectrodes. Dielectrophoresis can be used to collect and deposit metallic SWCNTs in a bundle or an otherwise functionally-effective configuration, the conductivity of which is selectively sensitive to hydrogen. Hydrogen produced by glucose oxidation, and the resulting electrometric change, is measured to quantify glucose concentration Results show high-sensitivity monitoring of one sort useful for non- or minimally invasive applications. For instance, an extremely small amount of a body fluid can be analyzed rather than whole blood in large quantity. Clinically important blood gases, such as $CO_2$ and $O_2$, do not influence sensor response nor does the presence of hydrogen ion, confirming high specificity. The inventive sensor and/or method(s) also demonstrated a quick response (about ≦10 sec) with simple detection (e.g., resistance change), and easy fabrication.

Benefits associated with gas sensing by SWCNTs include room temperature operation, simple configuration, quick response to analytes, and very low detection limit. While the conductivity of semiconducting SWCNTs changes in response to gases such as nitrogen, ammonia, oxygen, etc., metallic SWCNTs are known to be insensitive to such species. [P. G. Collins, K. Bradley, M. Ishigami, and A. Zettle, "Extreme Oxygen Sensitivity of Electronic Properties of Carbon Nanotubes," *Science*, vol. 287, pp. 1801–1804, 2000.]

It was recently predicted by quantum mechanical calculation that gas molecules could be strongly adsorbed into inter-tube interstitial spaces or sites of bundled or closely packed or configured SWCNTs. [J. Zhao, A. Buldum, J. Han, and J. P. Lu, "Gas molecule adsorption in carbon nanotubes and nanotube bundles," *Nanotechnology*, vol. 13, pp. 195–200, 2002.] The calculation also predicted that, due to size limitations, only hydrogen molecules would fit into the sites. Accordingly, providing a bundle of metallic SWCNTs, a conductivity change would occur upon sorption of hydrogen, but would not be significantly affected by other gas species. (See FIG. 1)

When glucose is oxidized by a glucose oxidase (GOD), $H_2O_2$ is produced as shown in equation (1). [See, e.g., A. E. G. Cass, *Biosensors: A Practical Approach*, Oxford University Press, New York, 1990.] Under a certain voltage potential, $H_2O_2$ can be further electrolyzed to yield oxygen and hydrogen. [See, Walter C. Schumb, Charles N. Satterfield, Ralph L. Wentworth, Hydrogen Peroxide, American Chemical Society Monograph Series, Chap. 8, Decomposition Processes, 1955, Reinhold Publishing Corporation, New York, N.Y.] The conductivity will change due to the adsorption of hydrogen in the interstitial sites of bundled metallic SWCNTs. More specifically, the charge transport capability of the SWCNTs will be reduced by the adsorption of hydrogen, resulting in an increase in the electrical resistance. Consequently, glucose concentration can be quantified by measuring or monitoring an electrometric change, as the hydrogen gas produced is proportional to the peroxide oxidation product and initial glucose concentration.

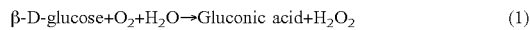

$$\beta\text{-D-glucose} + O_2 + H_2O \rightarrow \text{Gluconic acid} + H_2O_2 \qquad (1)$$

Accordingly, the present invention is directed, in part, to a glucose sensor. Such a sensor comprises an apparatus comprising a plurality of metallic single-walled carbon nanotubes arranged and configured to define at least one interstitial space or site for sorption of hydrogen gas, with at least one of the nanotubes positioned across and in electrical contact with an electrode pair; and (2) a glucose oxidase component in contact with or proximate to the nanotubes. As contemplated within the broader scope of this invention, the oxidase component can contact the nanotubes, be positioned thereon, thereabout or relative thereto sufficient to function at least in part as described herein. In addition to an oxidase enzyme, such a component can comprise a liquid-permeable portion and a gas-permeable portion, the former for introduction of a glucose-containing fluid medium to the component with the latter to facilitate passage of a resulting oxidation product (e.g., hydrogen peroxide). Glucose oxidase is commercially available and can be derived from a range of suitable biological sources.

The inventive sensor further comprises a voltage source providing a current sufficient to at least partially reduce physiologically or clinically-significant concentrations of hydrogen peroxide produced upon introduction of glucose to the oxidase component. An electrometer connected to the apparatus is responsive to hydrogen sorption on the nanotubes. Typically, an ohmmeter can be used; however, volt and amp meters can also be utilized given the interrelationship of such current parameters. Use of such a glucose sensor/apparatus can be evidenced by an oxidase component gluconic acid as a residual byproduct of glucose oxidation.

As inferred above, the present invention can also include a method of sensing glucose. Such a method comprises (1) providing an apparatus comprising a plurality of metallic single-walled carbon nanotubes with a voltage potential thereacross, the nanotubes arranged and configured to define at least one interstitial space and in contact with a glucose oxidase component; (2) introducing glucose to the oxidase component; and (3) monitoring electrical response upon interstitial sorption of hydrogen gas. In certain embodiments, such a response can comprise a change in conductive resistance of the nanotube. Alternatively, voltage or current change can be monitored upon hydrogen sorption, responsive to glucose introduction. Such a method can be utilized to detect glucose in a bodily fluid or diluted solution that has a sampled bodily fluid at broad range of concentrations that include the clinically significantly range of 1 mM to 10 mM. A very low detection limit (0.028 mM×10 µl) can be achieved when the smallest measurable resistance variation (11 µΩ/Ω) is considered in the current experimental data. Likewise, the methods of this invention are clinically useful in that regardless of glucose concentration, fluid volumes less than about 10 µL can be used with good effect.

Alternatively, the present invention can be considered as a method of using metallic single-walled carbon nanotubes to determine glucose concentration. Such a method comprises (1) providing a plurality of metallic single-walled carbon nanotubes defining at least one interstitial space, at least one of the nanotubes positioned across an electrode pair, having an electrical resistance and in contact with a glucose oxidase component thereon; (2) introducing glucose to the oxidase component; (3) applying a current across the electrode pair at least sufficient to produce hydrogen gas; and (4) determining a change in resistance upon glucose introduction. At the low glucose concentrations and fluid volumes typically utilized with this methodology, currents less than about 5 mA can be applied with good effect. As demonstrated below, the changes in resistance upon hydrogen sorption can be normalized then compared to a scale of standard glucose concentrations versus normalized resistance values, to determine a subject glucose concentration.

DETAILED DESCRIPTION OF CERTAIN EMBODIMENTS

Figure 2:
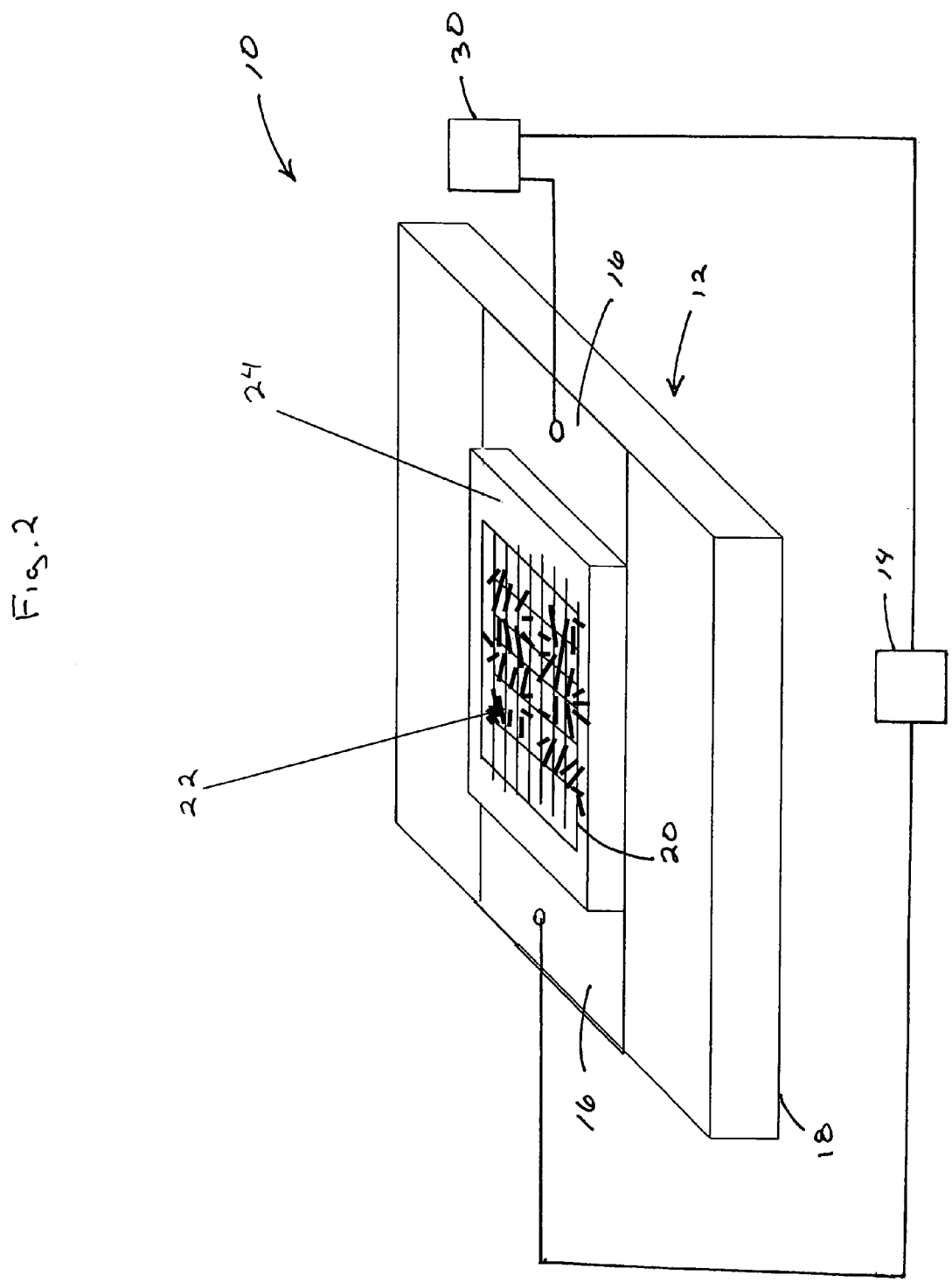
FIG. 2. A schematic diagram representing a glucose sensor and carbon nanotube apparatus, in accordance with this invention.

With reference to FIG. 2, in accordance with this invention, glucose sensor 10 can comprise apparatus 12, voltage source 14 in contact with electrodes 16 on substrate 18. As discussed elsewhere herein, electrodes 16 can be provided in a pattern 20 conducive for the deposition and placement of corresponding bundles or packed configurations of carbon nanotubes 22. In certain embodiments, electrodes 16 can comprise interdigitated comb pattern 20. (FIG. 3) Common circuit components connect electrodes 16, source 14 and electrometer (e.g., amp meter) 30. Voltage source 14 is incorporated with electrometer 30 where circuit resistance (e.g., ohmmeter) is determined/monitored.

Figure 4A:
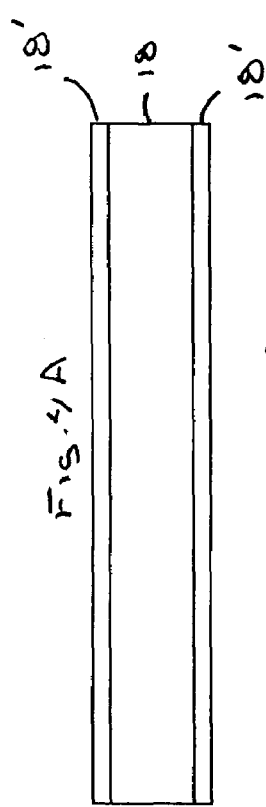
FIGS. 4A–G. With reference with FIG. 2, a schematic stepwise illustration showing fabrication of a sensor/apparatus, in accordance with this invention.
Figure 4B:
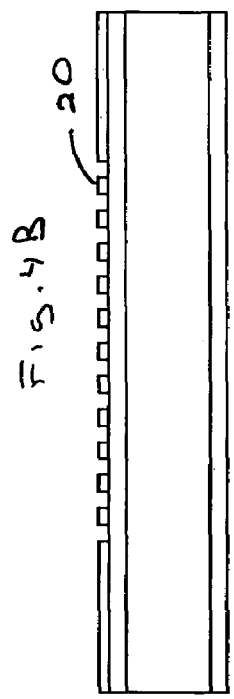
Figure 4C:
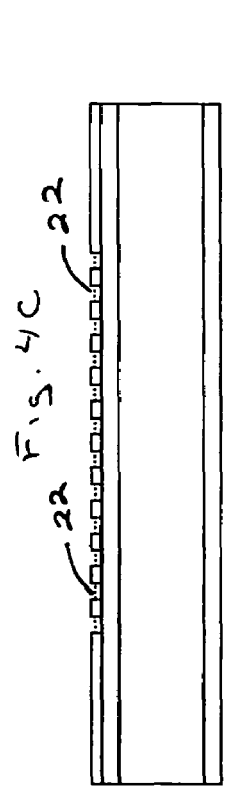
Figure 4D:
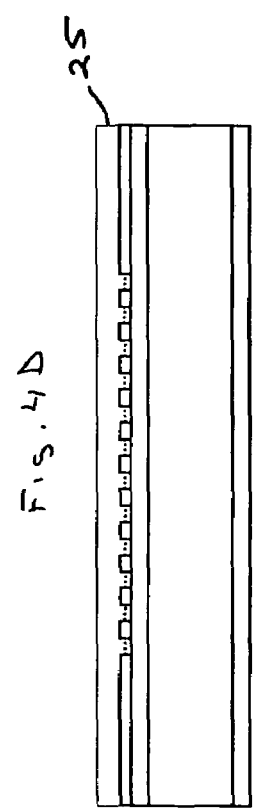
Figure 4E:
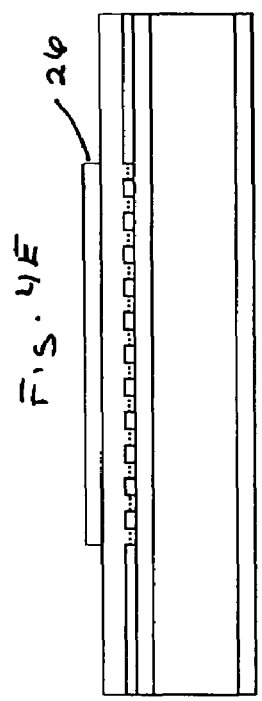
Figure 4F:
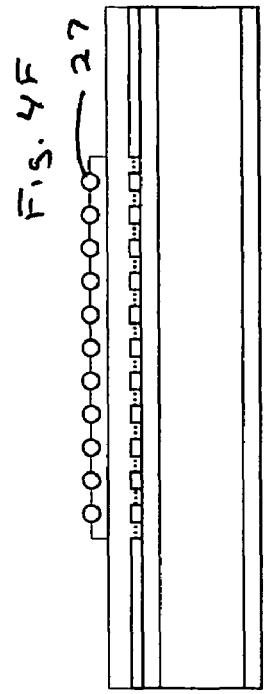
Figure 4G:
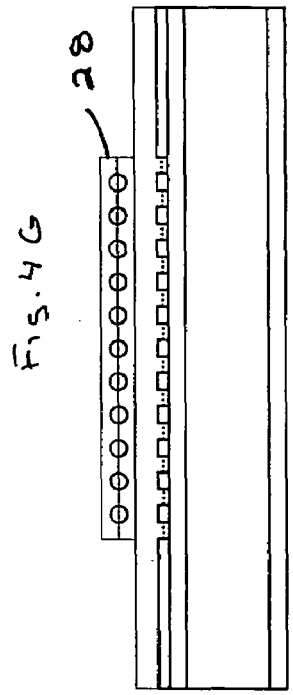

As discussed above, glucose oxidase component 24 contacts nanotubes 22. With reference to FIG. 4, such a component can comprise a gas permeable component 25 over nanotubes 22, electrodes 16 and, optionally, oxidized substrate 18' (FIG. 4A–D). Component 24 can further comprise liquid permeable portions 26 and 28 providing a matrix for glucose oxidase 27 (FIGS. 4E–G). See, also, Examples 1 and 2, below.

Figure 3:
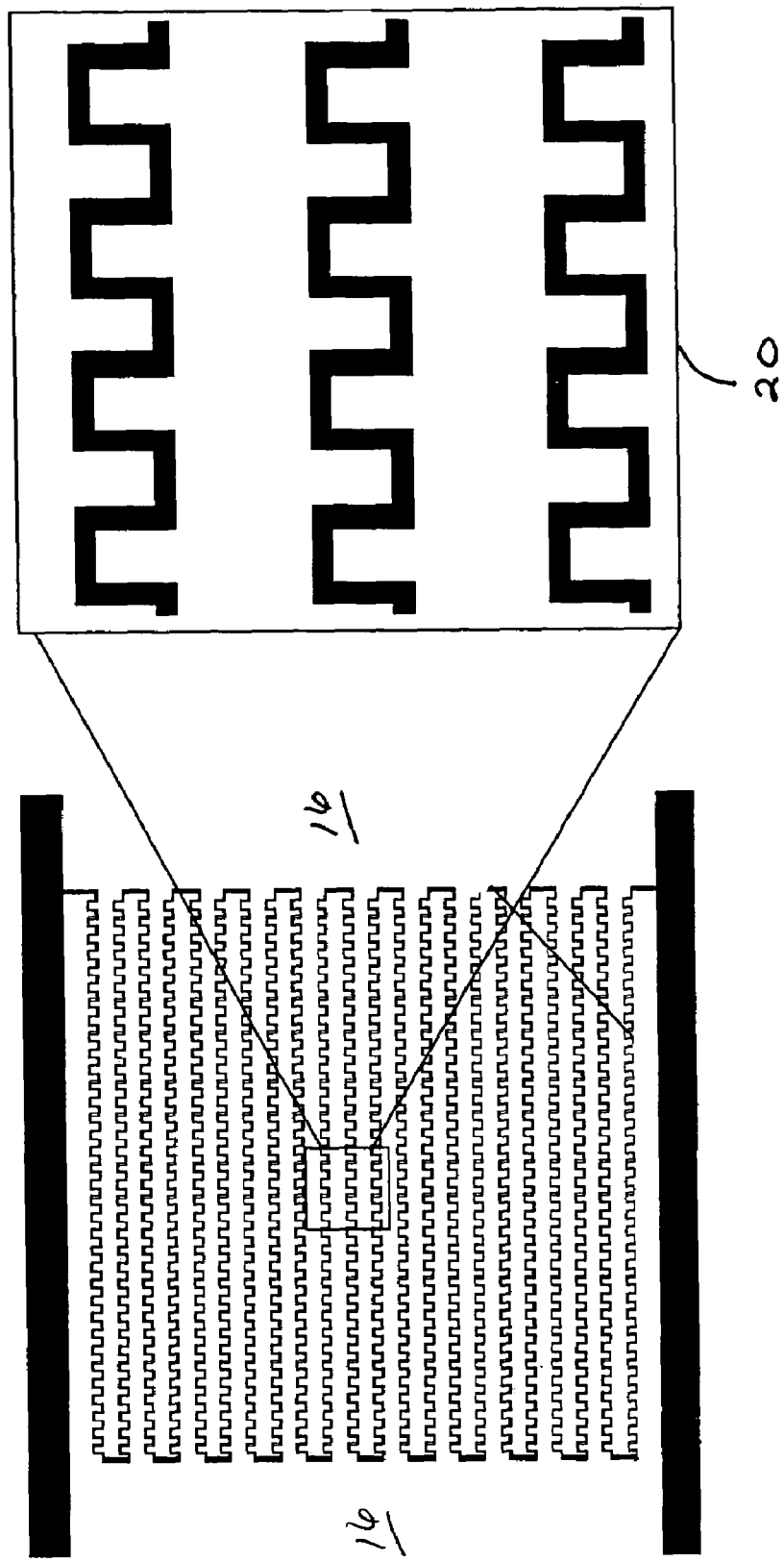
FIG. 3. A top view of a certain electrode configuration, as can be used in conjunction with the sensor/apparatus of FIG. 2.

With reference to FIG. 3, electrodes 16 are designed and patterned such that the gradient of the electric field produced maximizes the number of attracted SWCNTs on both electrodes. Under current conditions of the sort described herein, SWCNTs are attracted to and deposited at the inner edge of each electrode, a point of highest electric field gradient. When one or more SWCNTs are so positioned, a higher electrical field gradient is generated at the ends of each SWCNT, as the deposited resistance is much smaller than the contact resistance, presumably due to the Schottky barrier between the SWCNTs and the metal electrodes. Consequently, a larger dielectrophoretic force is formed locally to attract more SWCNTs, until the contact resistance becomes low enough to release the concentrated electric field. Without limitation to any one theory or mode of operation, the observed bundle or packed configuration of SWCNTs is believed to be formed spontaneously in this manner.

As described elsewhere herein, such a configuration of metallic SWCNTs, deposited on the electrodes, are capable of molecular hydrogen gas detection—believed due to size-exclusive sorption facilitated by interstitial sites or spaces defined by the nanotube configuration. Again, without limitation to any one theory or mode of operation, it is believed that hydrogen gas is generated by electrolysis of hydrogen peroxide, a glucose oxidation product. Likewise, without limitation, it is believed a gas phase electrolysis has at least a partial role in observed sensor function. Accordingly, circuit connection between electrodes does not necessarily involve SWCNTs of the bundled/packed configuration. Numerous nanotubes are without electrode contact. While a large electrical potential is present between the SWCNTs and the metal electrodes (the Schottky barrier), the nanotubes have low electrical conductivity. Gas-phase electrolysis (e.g., hydrogen peroxide) is believed to occur in the electrical contact region, with subsequent sorption (e.g., hydrogen) within interstitial spaces of the non-electrode contacting nanotubes. Results observed can be understood by analogy of the inter-electrode SWCNTs to a non-aqueous electrolyte of an electrochemical cell.

EXAMPLES OF THE INVENTION

The following non-limiting examples and data illustrate various aspects and features relating to the sensors, apparatus and/or methods of the present invention, including the use of single-walled carbon nanotubes for the detection or sensing of hydrogen gas produced via glucose oxidation. In comparison with the prior art, the present methods and sensors/apparatus provide results and data which are surprising, unexpected and contrary to the prior art. While the utility of this invention is illustrated through use of several apparatus configurations and chemical systems/components which can be used therewith, it will be understood by those skilled in the art that comparable results are obtainable with various other apparatus configurations and components, as are commensurate with the scope of this invention.

Example 1

It is known in the art that approximately 70% of grown SWCNTs have semiconducting characteristics, while the remaining approximate 30% have metallic characteristics. [R. Krupke, F. Henmich, H. v. Lohneysen, and M. M. Kappes, "Separation of Metallic from Semiconducting Single-Walled Carbon Nanotubes," *Science*, vol. 301, pp. 344–347, 2003.] According to the mechanism mentioned previously, however, the present invention comprises sufficient metallic SWCNTs in a nanotube population having a grouped or bundled configuration to effectively sense hydrogen. Dielectrophoresis can be used to collect SWCNTs with similar electrical (e.g., metallic) properties. As demonstrated below, a non-uniform electric field between a pair of electrodes induces an attractive dielectrophoretic forces on particles, e.g., SWCNTs, suspended in a suitable medium (e.g., dichlorobenzene solution). By the dielectrophoretic force at a specific frequency band (e.g., at 1 MHz), metallic SWCNTs can be selectively collected and deposited across a pair of electrodes. [R. Krupke, F. Henmich, H. v. Lohneysen, and M. M. Kappes, "Separation of Metallic from Semiconducting Single-Walled Carbon Nanotubes," *Science*, vol. 301, pp. 344–347, 2003; H. A. Pohl, *Dielectrophoresis*, Cambridge Univ. Press, Cambridge, 1978.] In contrast, a high-frequency electric field produces a negative (repulsive) dielectrophoretic force on semiconducting SWCNTs, and they are repelled from the electric field. When a metallic SWCNT is deposited across electrodes by dielectrophoresis, the electric field is deformed and concentrated at both ends of the SWCNT, presumably due to Schottky barriers between the SWCNT and metal electrodes. In this manner, many SWCNTs can be deposited in densely packed bundles.

Example 2

As mentioned above, FIGS. 2–4 show schematically the fabrication and structure of a glucose sensor and/or apparatus in accordance with this invention. Further details relating to substrate preparation and oxidation, electrode deposition and patterning, and corresponding lithographic techniques are provided in co-pending application Ser. No. 10/426,925, in particular Examples 16–17 and FIGS. 20, 23–26 thereof, filed Apr. 30, 2003, the entirety of which is incorporated herein by reference. Likewise, as would be understood by those skilled in the art, information relating to substrate, electrode and circuit preparation is also provided in the aforementioned and incorporated '020 patent, in particular columns 3–6 and by way of the figures referenced therein. More specifically, with reference to FIG. 5, SWCNTs (commercially, from HiPCo) individually separated and dispersed in 1,2-dichlorobenzene by sonication (38) were deposited on an oxidized Si substrate (32), as described above, on Cr/Au (100/800 Å) electrodes (34–40) by dielectrophoresis (electric field: 1.4V/μm@1 MHz). [P. Nikolaev, M. J. Bronikowski, R. K. Bradley, F. Rohmund, D. T. Colbert, K. A. Smith, R. E. Smalley, "Gas-phase catalytic growth of single-walled carbon nanotubes from carbon monoxide," *Chem. Phys. Lett.*, vol. 313, pp. 91–97, 1999.] The sample was annealed (42) at 200° C. to evaporate the solvent (b.p.: 180° C.). PDMS (polydimethylsiloxane, Sylgrad 184, Dow Corning Corp., Midland, Mich.) was prepared and spin-coated (44–46) at 3000 rpm for 3 minutes as a gas-permeable (non-permeable to liquid) membrane on the top of the SWCNT-deposited electrodes. The PDMS membrane was baked (48) on a hot plate (100° C.) for an hour. A hydrogel (pHEMA, 2-hydroxyethyl methacrylate) was patterned (50) under a UV radiation at 20 Watt/cm$^2$ for 8 minutes. GOD from *Aspergillus niger* (E.C.1.1.3.4, Sigma-Aldrich Corp., St. Louis, Mo.) was immobilized (52) by physical adsorption for 30 minutes (1000U/10 μL), and an additional hydrogel layer was patterned (54) to entrap and maintain the enzyme. [M. Y. Arica and V. Hasirci, "Immobilization of Glucose-Oxidase—a Comparison of Entrapment and Covalent Bonding," *J. Chem. Tech. Biotechnol*, vol. 58, pp. 287–292, 1993.] The fabricated sensor was kept (56) in a phosphate buffer (10 mM, pH 7.4) at 4° C. for further use. In accordance with this invention, various other substrate, electrode, oxidase and gas-/liquid-permeable components—providing comparable function—can be used herewith, as would be understood by those skilled in the art made aware of this invention.

Example 3

Even though the deposited SWCNTs were barely visible under scanning electron microscopy (SEM), the deposition result was confirmed by a finite resistance after deposition. The electrodes in FIG. 3 were designed and fabricated to have an interdigitated comb (i.e., a so-called "Ramen")

structure for a higher electric field gradient and maximum concentration of deposited SWCNTs. As expected, dielectrophoresis aggregated SWCNTs around the electrodes, due to a concentrated electric field. The deposited SWCNTs and porous structure of the GOD-immobilized hydrogel matrix can be observed via SEM.

Figure 6:
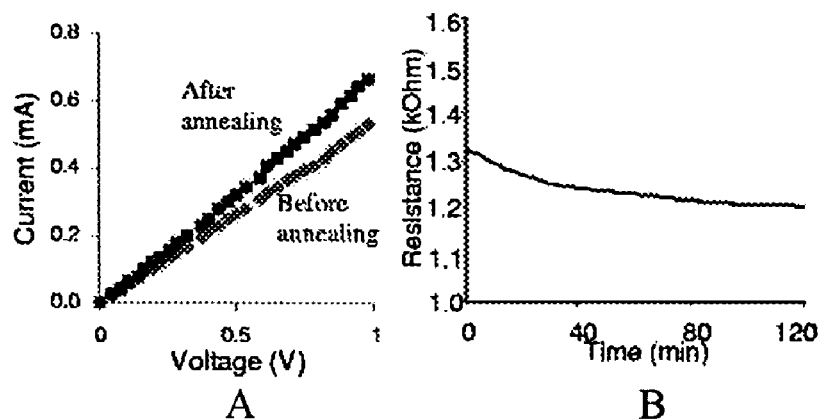
FIG. 6. Electrical characteristics of deposited SWCNTs (A) I–V curve on SWCNTs (B) Time profile of SWCNTs during resistance measurement.

When a resistance was measured right after the SWCNT deposition, the value was approximately ~2 kOhm. When the solvent was completely evaporated, a better electrical contact was made, and the resistance reduced to a half, ~1 kOhm. It was confirmed that the deposited SWCNTs have metallic characteristics as shown in FIG. 6A. During the measurement, the resistance decreased due to a slight temperature increase by the current used for measurement (FIG. 6B).

Example 4

Figure 7:
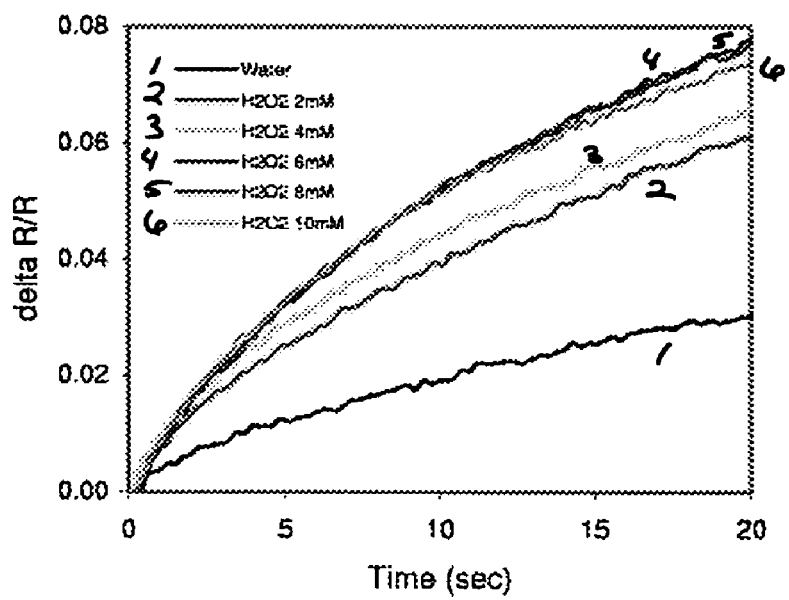
FIG. 7. Response to $H_2O_2$ (SWCNTs spin-coated with PDMS), in accordance with the methods and apparatus of this invention.

The response pattern of a fabricated sensor to $H_2O_2$ was evaluated [FIG. 7]. For purposes of this experiment, the GOD reaction layer was not necessary, and the device was coated only with PDMS. A droplet of $H_2O_2$ solution (10 μL) was placed above the SWCNT-deposited electrodes, and a resistance was monitored. Solutions of different concentrations were used including DI water and a series of diluted $H_2O_2$ (2, 4, 6, 8, 10 mM). After each droplet was applied, the resistance increased and reached a steady-state value. The normalized resistance change (ΔR/R) for the initial 10 seconds was related to the concentration of $H_2O_2$. The increase of the resistance reached a maximum at 6 mM and began to decrease at 8 mM. This observation is believed due to the self-decomposition of hydrogen peroxide at higher concentrations. The decomposition leads to generation of proton ions that caused a response shift in the opposite direction (vide infra), a condition resolved by controlling the density of deposited SWCNTs and the concentration of immobilized enzyme for a device with reaction layers.

Example 5

Figure 8:
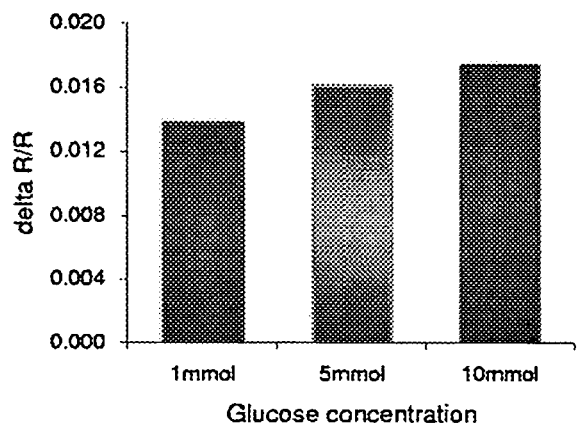
FIG. 8. $\Delta R/R$ on glucose concentration (at t=10 seconds).

Devices with whole reaction and diffusion layers integrated were used for testing glucose solutions at various concentrations. The normalized resistance change was measured at 10 seconds after the glucose solution (1, 5 and 10 mM) was placed on the device. FIG. 8 illustrates that the resistance increased according to the increase of glucose concentration. Concentrations much lower than 1 mM, can be readily measured as shown in the trend of the graph. In principle, a very low detection limit (less than about 0.028 mM×10 μl) can be achieved as smaller measurable resistance variations (e.g., less than about 11 μΩ/Ω) are considered.

Example 6

Figure 9:
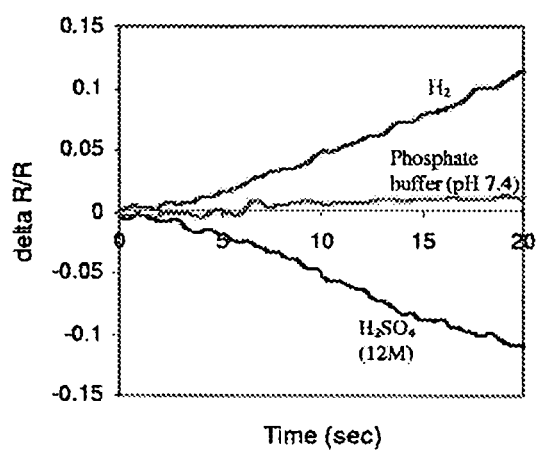
FIG. 9. Response of SWCNTs on Buffer, $H_2SO_4$, and $H_2$.
Figure 10:
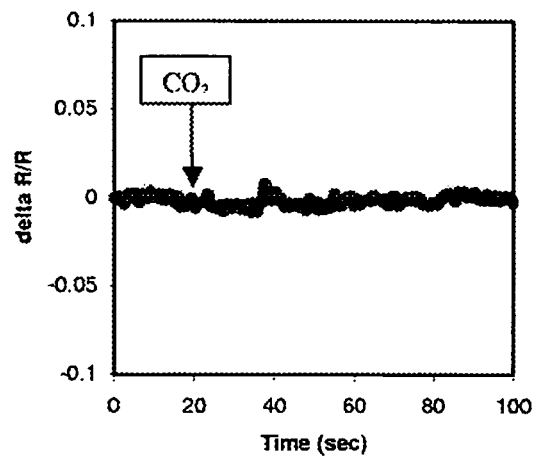
FIG. 10. Response($\Delta R/R$) to $CO_2$ (1M).

The sensor/apparatus responded insignificantly to other gases or chemical species produced as a result of the GOD reaction or as can exist in a blood sample (e.g., hydrogen ion, $O_2$ and $CO_2$, FIG. 9). An extremely high concentration (1M) of bicarbonate ion ($HCO_3^-$), carrying $CO_2$ and hydrogen ion in blood, did not cause any response change (FIG. 10), indicating a physiological increase in $pCO_2$ or pH appears not to influence the sensor performance. Protons caused the signal to decrease only at an abnormally high concentration (e.g., $H_2SO_4$, 12M). For the phosphate buffer (pH 7.4), the resistance ratio increased a little possibly owing to diffusion of $H_2$ molecules. When the device was placed in a chamber with $H_2$ only, the resistance drastically increased as expected.

Example 7

Figure 11:
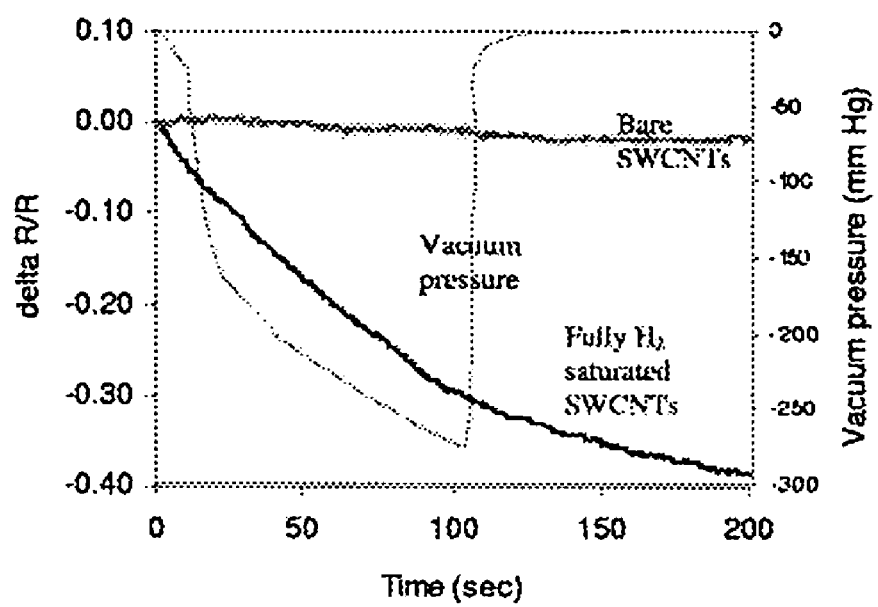
FIG. 11. Response of fully $H_2$ saturated and bare SWCNTs.

The effect of exposure to air (i.e., oxygen and nitrogen) was also tested. FIG. 11 shows that an abrupt increase or decrease of air concentrations using a repeated evacuation process had no effect on the sensor signal. A fully $H_2$ saturated SWCNTs that had been placed in a buffer solution for a few hours showed a signal decrease due to the time-dependent depletion of hydrogen molecules from the interstitial sites when subsequently placed in air or in vacuum However, the SWCNTs in this case did not respond to air concentration. These results confirm that neither oxygen nor nitrogen affect the electrometric response of or charge transfer process associated with a metallic SWCNT configuration of this invention.

While the principles of this invention have been described in connection with specific embodiments, it should be understood clearly that these descriptions are added only by way of example and are not intended to limit, in any way, the scope of this invention. For instance, the present invention can be applied more specifically to a range of other possible analytes and/or enzymatic systems producing, directly or indirectly, hydrogen gas or hydrogen peroxide. Regarding the latter, however found or generated, it was often important to quantify its concentration at low levels. The apparatus and method(s) of this invention may be used in conjunction with bioassays as an alternative to the hydrogen peroxidase systems currently employed. Likewise, as would be understood by those skilled in the art, the present invention can be utilized in conjunction with the retention or storage of hydrogen, for subsequent use or application. Other advantages, features and benefits of this invention will become apparent from the claims hereinafter, as would be understood by those skilled in the art.

We claim:

1. A method of sensing glucose, said method comprising:
providing an apparatus comprising a plurality of metallic single-walled carbon nanotubes with a voltage potential thereacross, said nanotubes arranged and configured to define at least one interstitial space and contacting a glucose oxidase component;
introducing glucose to said glucose oxidase component; and
monitoring electrical response upon interstitial sorption of hydrogen gas.

2. The method of claim 1 wherein said glucose is in a fluid medium at a concentration greater than about 1 mM.

3. The method of claim 2 wherein said medium has a volume less than about 10 μL.

4. The method of claim 2 wherein said medium comprises a bodily fluid.

5. The method of claim 1 wherein said glucose oxidase is of a bacterial origin.

6. The method of claim 1 wherein said response is a change in resistance of said nanotubes.

7. The method of claim 1 wherein glucose is oxidized to gluconic acid.

* * * * *